United States Patent
Huemer

(10) Patent No.: US 8,279,433 B2
(45) Date of Patent: Oct. 2, 2012

(54) HAEMOLYSATOR

(75) Inventor: Herfried Huemer, Feldbach (AT)

(73) Assignee: Roche Diagnostics Operating, Inc., Indianapolis, IN (US)

( * ) Notice: Subject to any disclaimer, the term of this patent is extended or adjusted under 35 U.S.C. 154(b) by 322 days.

(21) Appl. No.: 12/616,930

(22) Filed: Nov. 12, 2009

(65) Prior Publication Data

US 2010/0151512 A1 Jun. 17, 2010

(30) Foreign Application Priority Data

Nov. 12, 2008 (EP) .................................... 08450180

(51) Int. Cl. *G01N 1/10* (2006.01)

(52) U.S. Cl. .......... 356/246; 356/39; 356/326; 310/311; 310/366

(58) Field of Classification Search .................... 356/39, 356/246, 326; 310/311, 366, 328, 348, 353
See application file for complete search history.

(56) References Cited

U.S. PATENT DOCUMENTS

| | | | |
|---|---|---|---|
| 3,972,614 A | 8/1976 | Johansen et al. | |
| 5,757,482 A * | 5/1998 | Fuchs et al. | 356/246 |
| 5,869,767 A | 2/1999 | Hayward et al. | |
| 6,100,084 A | 8/2000 | Miles et al. | |
| 6,307,306 B1 | 10/2001 | Bast et al. | |
| 6,686,195 B1 * | 2/2004 | Colin et al. | 435/306.1 |
| 6,739,531 B2 | 5/2004 | Taylor | |
| 7,948,619 B2 * | 5/2011 | Huemer | 356/246 |
| 2008/0308404 A1 * | 12/2008 | Luotola et al. | 204/157.15 |
| 2009/0079300 A1 * | 3/2009 | Hielscher et al. | 310/324 |

FOREIGN PATENT DOCUMENTS

| | | |
|---|---|---|
| DE | 199 30 585 A1 | 2/2000 |
| EP | 1764608 A2 | 3/2007 |
| GB | 2 403 729 A | 1/2005 |

OTHER PUBLICATIONS

Taylor, et al., Disrupting Bacterial Spores and cells using Ultrasound Applied through a Solid Interface, $2^{nd}$ Annual International IEEE-EMBS Special topic conference on Microtechnolgies in medicine & Biology (2002).

* cited by examiner

Primary Examiner — Layla Lauchman
(74) Attorney, Agent, or Firm — McDonnell Boehnen Hulbert & Berghoff

(57) ABSTRACT

A haemolysator having a sonotrode plate and oscillation generating elements acting thereupon, wherein the oscillation generating elements are set into mechanical oscillations by an electrical AC-signal generator. The haemolysater also includes a sample chamber to which the sonotrode plate transmits mechanical oscillations, and has oscillation generating elements that are excitable toward mechanical oscillations in a wide frequency band.

24 Claims, 5 Drawing Sheets

PRIOR ART

HAEMOLYSATOR

CROSS REFERENCE TO RELATED APPLICATION

This application claims priority to European Patent Application No. 08450180.8, filed Nov. 12, 2008.

BACKGROUND OF THE INVENTION

1. Field of the Invention

The invention relates generally to a haemolysator, and in particular, a haemolysator in combination with a cuvette (measuring chamber) for receiving a sample. The invention also relates to a spectroscopic analyzer comprising a haemolysator. Furthermore, the invention relates to an oscillation system comprising multilayer actuators and in particular to a haemolysator comprising multilayer actuators. The invention also relates to a process for the function testing and monitoring of the operating state of a haemolysator equipped with piezoelectric multilayer actuators.

2. Description of Related Art

A haemolysator as initially mentioned is used in a spectroscopic analyzer, in particular for the spectroscopic determination of haemoglobin derivatives, e.g., $O_2Hb$, HHb, COHb, MetHb and quantities derived therefrom (oximetry and co-oximetry, respectively). However, the haemolysator is also suitable for use in combined spectroscopic-chemical analyzers. Said analyzers serve, among other things, for the decentralized determination of blood gases ($O_2$, $CO_2$, pH), electrolytes ($K^+$, $Na^+$, $Ca^{++}$, $Cl^-$), metabolites (glucose and lactate), haematocrit, haemoglobin parameters (tHb, $SO_2$, etc.) and bilirubin in whole-blood samples. In doing so, characteristic photometric absorption properties of those substances are utilized and measured values are evaluated via a mathematical algorithm.

In order to be able to achieve the required measuring accuracy, a haemolysis of the whole blood is necessary prior to the optical measurement, which haemolysis is performed by means of the haemolysator. In doing so, the blood cells are destroyed mostly by ultrasonic energy in order to be able to conduct the measurement without interfering light scattering effects.

In FIG. 1, a schematic diagram of an oximeter module 200 of a spectroscopic analyzer is illustrated, with the oximeter module being known from the prior art. Said oximeter module comprises a source of measuring light 201 which generates a beam of light 202 which is concentrated by a lens 203 and directed onto an optical measuring chamber 204. Said optical measuring chamber 204, which is also referred to as a "cuvette", has transparent case walls through which the beam of light 202 can pass. A sample 205, in particular a whole-blood sample, having characteristic photometric absorption properties which change the spectral composition of the beam of light 202 passing through the sample is located in the measuring chamber 204. After leaving the measuring chamber 204, the beam of light 202 is introduced into an optical waveguide 206 and guided to a spectroscopic sensor 207. The spectroscopic analysis of the sample 205 requires a haemolysis in which the blood cells in a whole-blood sample are destroyed by ultrasound so that the sample is transformed into a liquid which does not substantially scatter the beam of light 202. The haemolysis is performed by means of a haemolysator 210 desiged as an ultrasonic transducer and comprising piezoceramic elements 211 which generate mechanical oscillations via excitation by electrical alternating current signals due to the reverse piezo effect (i.e., the physical phenomenon in which mechanical deformations are caused by applying electrical signals to a piezo element), which mechanical oscillations are transmitted to a resonator 212 and amplified (see also FIG. 2). The resonator 212 in turn transmits the mechanical oscillations via a coupling surface 213 formed on its front side to a case wall of the measuring chamber 204, whereby the oscillations propagate into the sample 205 and cause the blood cells to burst therein due to cavitation effects. Furthermore, the haemolysator 210 has a counter weight 214 arranged on the side of the piezoceramic elements 211 which faces away from the resonator 212. In order that the measuring chamber 204 is not destroyed by the mechanical oscillations and in order to ensure an appropriate propagation of the mechanical oscillations into the sample 205, the measuring chamber must be mounted elastically. This is effected by a spring washer 215 which prestresses an anvil 216 against the side of the measuring chamber 204 which faces the haemolysator 210.

According to the prior art, haemolysators 210 of the ultrasonic transducer type have so far been configured as resonance oscillators which are prompted to oscillate by an electrical sinusoidal signal at the resonance frequency inherent to the haemolysator. The ultrasonic transducer haemolysator 210 illustrated in FIG. 2 is such a prior art haemolysator 210 based on the resonance oscillator principle.

Spectroscopic analyzers comprising haemolysators according to the resonance oscillator principle are known, for example, from U.S. Pat. No. 3,972,614.

A disadvantage of known haemolysators of the resonance oscillator ultrasonic transducer type is their considerable overall length which has to be dimensioned such that a maximum oscillation amplitude is achieved in the sample position. The resonance oscillator ultrasonic transducer is a $\lambda/2$-oscillator which requires an overall length of a few cm (typically approx. 10 cm). This results in bulky analyzers.

Furthermore, the resonance oscillator must have a very high quality because of its action principle of excitation at resonance frequency, which leads to the fact that it can be operated only in an extremely narrow frequency range. Firstly, this limits the control possibilities of the haemolytic process, since cavitation bubbles of different sizes and densities develop in the blood sample depending on the ultrasonic frequency. Secondly, in case of replaceable measuring chambers (cuvettes) in which haemolysis is to be performed, the problem which arises is that of different material and oscillation properties which are variable throughout the lifetime. If mechanical oscillations are transmitted by a resonance oscillator ultrasonic transducer—which, due to its principle, has been adjusted to a fixed frequency—the result will be that maladjustments might occur in the frequency behaviour, which would result in an insufficient haemolysis of the blood sample in the cuvette. Thirdly, it would also be beneficial to be able to perform quality controls and system tests during operation, but resonance oscillators with their very narrow useful frequency range are likewise unsuited for this.

Finally, the relatively high energy consumption of known resonance oscillator ultrasonic transducers is also problematic.

Accordingly, the inventors have identified a need in the art to provide a haemolysator for an oximeter module of a spectroscopic analyzer which is small and quiet, has a low energy consumption of $<=15$ W continuous power, can be subjected to internal quality checks, allows the system to remain operable even if the cuvette is exchanged, which changes the oscillation properties of the system, and performs a complete haemolysis of the blood sample.

SUMMARY OF THE INVENTION

It is against the above background that the present invention provides certain unobvious advantages and advancements over the prior art.

Although the present invention is not limited to specific advantages or functionality, it is noted that the present invention provides a haemolysator having a sonotrode plate that transmits mechanical oscillation to a sample chamber, and an oscillation generating element that is set into mechanical oscillations by an electrical AC-signal generator and is excitable toward mechanical oscillations in a wide frequency band, for example 20-50 kHz. In particular embodiments of the invention, the oscillation generating element may be tunably excitable, and the oscillation generating element may be excitable toward mechanical oscillation while being adjustable in its stroke amplitude.

In another aspect, the haemolysator of the invention has an exchangeable cuvette that is insertable into the sample chamber, wherein the cuvette has a sample channel for receiving a sample to be haemolysed, and the channel has at least one oscillation-transmitting wall resting against the sonotrode plate when the cuvette is inserted into the sample chamber.

In a further aspect, the haemolysator has two transparent elements that are spaced apart from each other to define two opposing boundary surfaces of the sample channel and at least one sealing element defining side walls of the sample channel. In a particular embodiment, the sample channel is closed in the longitudinal direction and comprises an inlet and an outlet, and at least one spacer keeps the transparent elements apart from each other. One of the two transparent elements may have a shoulder extending in the direction toward the other transparent element and forms a boundary surface of the sample channel so that the height of the sample channel is smaller than the height of the at least one spacer.

In various aspects of the invention, the cuvette is integrated in a consumable of a spectroscopic analyzer, such as a fluid pack comprising functional liquids and/or waste containers.

In one particular aspect, the oscillation generating element of the haemolysator of the invention is a piezoelectric multilayer actuator and the electrical AC-signal generator generates non-sinusoidal signals, for example freely definable waveforms and/or signals tunable in frequency.

Still further, the piezoelectric multilayer actuator may be clamped between a first and a second conductor and further includes electrically conductive mats arranged at the interfaces between the piezoelectric multilayer actuator and the conductors. In this aspect, the include particles of an electrically conductive material, such as carbon.

Another aspect of the invention is directed to a spectroscopic analyzer for the spectroscopic analysis by irradiating a sample with a beam of light and detecting the spectrum of the beam of light after it has passed through the sample, wherein the a sample located in a cuvette that is at least partially transparent. The analyzer comprising the haemolysator of the invention to haemolyse the sample.

In a further aspect, the invention is directed to an oscillation system having at least one oscillation generating element in the form of a piezoelectric multilayer actuator that is clamped between a first and a second conductor, and having electrically conductive mats arranged at interfaces between the multilayer actuator and the conductors. The mats include particles of an electrically conductive material, such as carbon, and may exhibit a resistance with negative temperature coefficients.

Still further, the invention is directed to a process for operating the haemolysator of the invention. The process includes tuning a piezoelectric multilayer actuator of the haemolysator from 20 to 50 kHz. The piezoelectric multilayer actuator may be excitable toward mechanical oscillations and is a sensor for detecting and evaluating a physical parameter associated with a piezo effect, such as the fading-out of the sonotrode plate after the electrical signal supply has been switched off. As an example, the fading-out manifests itself in the generation of an electrical voltage signal by the multilayer actuator.

The process of the invention may include the determination of a centre frequency the electrical voltage signal generated by the multilayer actuator. The determination of the centre frequency may use Fast Fourier Transformation.

In another aspect of the process of the invention, the detected physical parameter is the electrical capacity of the multilayer actuator or a mechanical force that acts upon the multilayer actuator and is determined by measuring the electrical voltage generated by the multilayer actuator. The haemolysator may initiate an alarm or error correction if a detected physical parameter lies outside of a predetermined operating range.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE FIGURES

The following detailed description of the embodiments of the present invention can be best understood when read in conjunction with the following drawings, where like structure is indicated with like reference numerals and in which.

Figure 1:
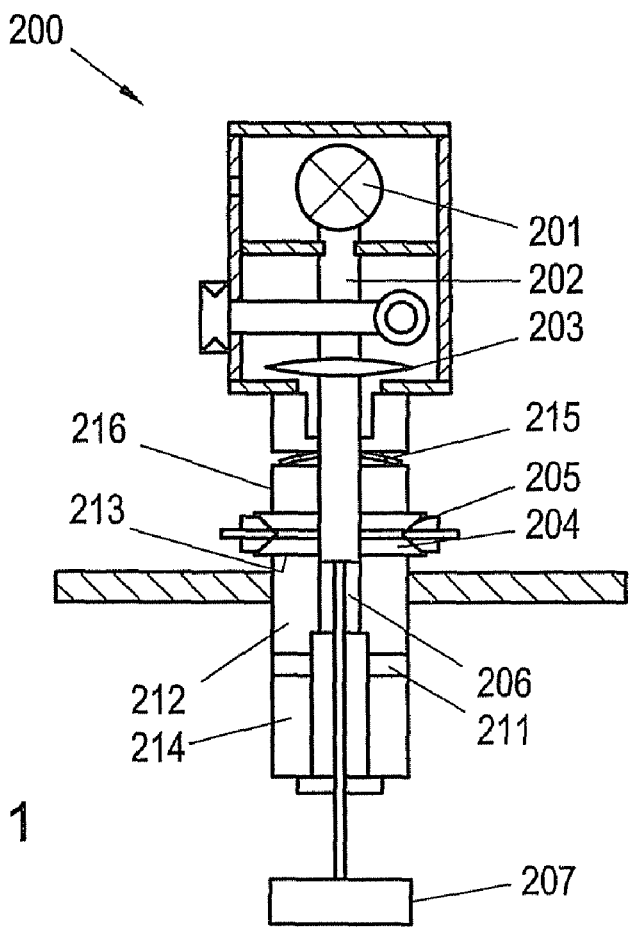
FIG. 1 shows a schematic diagram of a prior art oximeter module of a spectroscopic analyzer.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION

Before describing the present invention in detail, a number of terms will be defined. As used herein, the singular forms "a," "an", and "the" include plural referents unless the context clearly dictates otherwise.

The haemolysator according to the invention comprises a sonotrode plate and oscillation generating elements acting thereupon, wherein the oscillation generating elements can be set into mechanical oscillations by an electrical AC-signal generator, and a sample chamber to which the sonotrode plate transmits mechanical oscillations. According to the invention, the oscillation generating elements are excitable toward mechanical oscillations in a wide frequency band, and in one embodiment, for example in a variable way. The term "excitable in a wide frequency band" should be understood to mean that, on the one hand, oscillations which are broad-band due to their signal form can be generated and, on the other hand, oscillations which are narrow-band within the wide frequency band, e.g., sinusoidal oscillations with a discrete frequency, can also be generated. In one embodiment of the invention, it is envisaged that (narrow-band) oscillations are tuned through the broad-band frequency band.

Suitable frequency ranges in terms of the present invention are, in general, all frequency ranges in which a haemolysis caused by ultrasound can occur. In particular, these are frequency ranges which may cause a formation of cavitation bubbles in the medium due to ultrasound, which in turn might bring about the destruction of the cells contained in the medium.

In various embodiments, the frequency ranges are from 20-50 kHz. Lower frequency ranges are also possible, but involve the drawback that perceptible noise phenomena may occur due to a crossover with the audible frequency spectrum. Higher frequency ranges are likewise possible, but involve the drawback that high losses of energy and smaller efficiencies, respectively, may occur, for example, as a result of the heating of the haemolysator.

Thus, it is the basic concept of the present invention to provide a haemolysator which is not based on the resonance oscillator principle ($\lambda/2$ resonator which is excited by piezo elements), which, due to its principle, generates very narrow-band and non-variable mechanical oscillations, but instead comprises an ultrasonic transducer which exhibits mechanical oscillation generating elements which, being variable in a wide frequency band, can be excited toward mechanical oscillations by electrical alternating signals. With the aid of such broad-band mechanical oscillation generating elements, it is possible to regulate the excitation thereof in a stroke amplitude and stroke frequency such that the haemolysator will remain operable even if the internal oscillation properties of the system (for example, after the exchange of assembly groups such as cuvettes) change. The invention, therefore, is suitable for an embodiment in which the cuvette constitutes a consumption material or is a component of a consumer item, which is in the following also referred to as a "consumable", wherein it is a characteristic feature of such a consumable that it is replaced regularly. During the exchange of such consumables it has to be accepted that, due to inevitable variations in material properties between different batches of consumables, the mechanical and material properties of the replacement cuvettes integrated therein are not always exactly the same.

Ideally, analyzers comprising the haemolysator according to the invention should be operable easily and intuitively also for the "untrained" user. A further demand made on such a device is that it should be operable "almost without maintenance" from the user's point of view. "Almost without maintenance" is generally understood to mean that also a (technically) untrained user will replace consumption materials which merely exist in the form of cassettes and/or modules for a continuous operation. All consumption materials (consumables) should be exchangeable regularly by the user by simple intuitive manipulations, for example, after the expiry of a certain period of use or after a certain number of measurements have been obtained or after the resources provided therein have been consumed.

In prior art systems, such as described, e.g., in U.S. Pat. No. 3,972,614, the optical measuring chamber (cuvette) was designed as an integral component of the oximeter which remains permanently in the device. The analyzer described in U.S. Pat. No. 3,972,614 for the spectroscopic determination of parameters in blood samples such as, e.g., haemoglobin also comprises means for the ultrasonic haemolysis of the blood sample, i.e., the destruction of red blood cells, in order to render the blood sample as free from diffusers as possible. Only this will permit a precise spectroscopic analysis of the sample.

However, the high risk of clogging during the planned period of use is a disadvantage of the known system, wherein in particular the fluidic coupling points as well as a small layer thickness of the sample channel represent problematic issues. If contaminations or cloggings appear in such oximeter systems in the area of the cuvette, those can often be eliminated only by a costly exchange of the cuvette. In most cases, adequate training or the requirement of a service engineer is necessary for this purpose so that relatively long unplanned downtimes of the analyzer will often be the result. Furthermore, the manual exchange of a cuvette in such systems often requires subsequent manual adjustment and calibration steps in order to obtain reproducible measuring results.

As has already been explained above, the haemolysator according to the invention is, due to its flexibility in the electrical triggering, its variability in a stroke amplitude and stroke frequency, excellently suitable for analyzer systems in which the haemolysis is performed directly in exchangeable cuvettes, in particular for analyzer systems in which cuvettes are used which are replaceable easily and intuitively also for an "untrained" user, for example, because the cuvettes are part of a consumable which can be replaced regularly. Such an embodiment of the haemolysator according to the invention is characterized in that an exchangeable cuvette is insertable into the sample chamber, which cuvette exhibits a sample channel for receiving a blood sample, which channel is delimited by at least one oscillation-transmitting wall, with the oscillation-transmitting wall of the cuvette resting against the sonotrode plate in the inserted state.

The invention also relates to a combination of the haemolysator according to the invention with a cuvette, with the cuvette comprising at least one sealing element and two transparent elements, wherein the two transparent elements are spaced apart from each other and define two opposing boundary surfaces of a sample channel and the at least one sealing element defines side walls of the sample channel, whereby the sample channel is designed as a channel closed in the longitudinal direction and comprising an inlet and an outlet. At least one spacer is provided which keeps the transparent elements apart from each other. At least one of the two transparent elements has a shoulder extending in the direction toward the other transparent element and forming a boundary surface of the sample channel so that the height of the sample channel is smaller than the height of the at least one spacer.

By providing the shoulder on at least one of the two transparent elements, a well-defined height of the sample channel can be achieved, which is smaller than the height of the spacer, e.g., has a height of 0.1 or 1 mm. However, both the two transparent elements and the spacer are designed as solid elements of a sufficient thickness in order to be able to display the excellent mechanical stability and dimensional accuracy which are required and in order to be suitable for an ultrasonic haemolysis.

In order that the spacer maintains a satisfactory dimensional accuracy throughout its lifetime also in ultrasonic applications, the spacer can be manufactured from an injection-mouldable synthetic material having high modulus of elasticity values of, for example, more than 2500 MPa, or as an another example, more than 5000 MPa.

In one embodiment of the cuvette with excellent mechanical strength and dimensional accuracy, the transparent elements are glued to the spacer by means of a dimensionally stable adhesive which exhibits a defined layer thickness. A precise height of the sample channel can be set by adjusting the position of the transparent elements prior to the curing of the adhesive.

In an alternative embodiment, the transparent elements of the cuvette are moulded, stuck or connected by clamps to the spacer. Also in this embodiment, a high shape accuracy is achieved if the individual parts are mechanically processed prior to the assembly with such preciseness that the required narrow fitting tolerances are observed.

The sealing element rests planely against walls of the shoulders of the transparent elements. In order to prevent an amount of the sample from entering into possibly existing small clearances between the transparent elements and the sealing element due to the capillary effect on the interface, it is envisaged that the sealing element between the transparent elements is allowed to project into the sample channel. This is achieved by using a sealing element made of an elastic material, for example a material having a Shore D-hardness of between 50 and 80, or as another example, a Shore D-hardness of between 60 and 70, and pressing said sealing element against the transparent elements. Due to the flexibility of the material of the sealing element, said element is forced into the gap between the transparent elements and forms a sealing bead in the gap. The formation of the sealing bead can be promoted by providing the transparent elements with a radius or a chamfer at their edges facing the gap. So-called "sample carry-overs", i.e., the contamination of a sample by remnants of earlier samples in the cuvette and the falsification of reference measurements, respectively, are avoided in this way.

In another embodiment, the sealing element and the spacer fault a combination element, e.g., a 2-component injection-moulded part or a composite pressed part. By means of such a combination element, the assembly of the cuvette is substantially simplified and yet excellent strength and tightness are achieved.

One embodiment of the cuvette comprises transparent elements made of glass, for example, a pressed glass. This embodiment is characterized by its good producibility and high dimensional accuracy.

As an alternative to glass, a synthetic material having the following properties can be used for the transparent elements: low strain birefringence, minor creep behaviour, no/low gas permeability, chemical resistance, thermostability, optical transparency in the visible (VIS) and near infrared (NIR) wavelength ranges. The visible range (VIS) is defined as the wavelength range between 380 and 780 nm; the near infrared range (NIR) is between 780 and 1400 nm. In one aspect, the transparent elements are composed of synthetic materials from the group of thermoplastic olefin polymers.

The selection of the material of the transparent elements from the above-listed materials also permits thermostatting of the sample in the cuvette. In particular, blood samples have to be kept as precisely as possible at 37° C. during the spectroscopic analysis, since the spectra are temperature-dependent.

If the cuvette is integrated in a consumable (consumer item) of the spectroscopic analyzer, especially in a fluid pack comprising functional liquids (for example, calibration liquids, reference liquids, cleaning or standby liquids or also reagent liquids) and/or waste containers, the cuvette exchange will be easy and intuitive also for an "untrained" user, as it occurs in one operation with the replacement of the consumable.

The inventor has surprisingly found that, for the haemolysator according to the invention, piezoelectric multilayer actuators are suitable as mechanical oscillation generating elements. Those multilayer actuators fulfill the conditions of being variably excitable in a wide frequency band by electrical alternating signals. Multilayer actuators have already been used in injection systems in the automobile field, where they are used, however, under operational conditions which are completely different from those of the haemolysators according to the invention. The use of multilayer actuators in medical devices for haemolysis is unknown. By means of piezoelectric multilayer actuators, large oscillation amplitudes can be achieved in the haemolysator according to the invention without employing the resonator principle, and the overall size of the haemolysator can be drastically reduced.

In the haemolysator according to the invention, the piezoelectric multilayer actuators are integrated in a spring-mass system whose dimensioning can be adapted to the respective conditions. The use of multilayer actuators requires specific operational conditions (pretensioning forces, pulse shapes of the triggering). For optimizing their lifetime, a "gentle" operating mode which causes no damage to the material and/or suitable materials have to be chosen. For example, amplitudes, operating frequency, resonance frequency or also the ceramic compositions used can be appropriately chosen for this purpose. In contrast to the resonance principle, a non-sinusoidal pulse shape, which optionally is variable in frequency, may also be selected for the haemolysation of the blood, whereby the haemolysis and purification of the system can be optimized. Examples of applicable signal forms comprise, besides sinusoidal signals, also square-wave, triangle, sawtooth and pulse signals, but drive signals with freely definable waveforms are allowable as well.

In summary, the haemolysator according to the invention comprising piezoelectric multilayer actuators has the following features and advantages over the known resonance oscillator:
- a variable system in a stroke amplitude and stroke frequency,
- improvement of the haemolysation and purification with non-sinusoidal pulses and possibility of varying the pulse shape, frequency and amplitude,
- lower drive voltages are required,
- function testing and monitoring of the operating state of the multilayer actuators and hence of the haemolysator by monitoring the electrical parameters,
- a substantially smaller construction,
- use of the multilayer actuators as a sensor (force measurement, permanent detection of optimum operational conditions), particularly in combination with a replaceable cuvette.

A problem associated with multilayer actuators is posed by their contacting for an electrical connection to an electrical signal generator. Due to the relatively high electrical capacity of the multilayer actuators and their triggering with electrical signals in the kHz range, high currents (up to 10 A) flow across the contacting. Another difficulty which has to be overcome in the contacting is that the multilayer actuators change their thickness when they oscillate. However, the present invention also provides a solution to this problem, which is generally applicable in oscillation systems comprising multilayer actuators and in particular in a haemolysator comprising multilayer actuators. A general oscillation system according to the invention comprising at least one piezoelectric multilayer actuator is characterized in that the at least one piezoelectric multilayer actuator is clamped between a first and a second conductor, with electrically conductive mats being arranged at the interfaces between the multilayer actuator and the conductors, the mats containing particles of an electrically conductive material, in particular carbon.

The electrically conductive mats comprising the carbon particles typically exhibit a resistance with negative temperature coefficients which thus bring about an improved current conduction in particular at increasing temperatures, which is caused by the heating of the haemolysator during its operation. The carbon particles lie tightly on the surfaces of the conductors and the multilayer actuators, whereby, e.g., a double enlargement of the area active for the current conduction is achieved. Another advantage is that the electrically conductive mats are very flexible so that—in contrast to rigid connections such as soldered joints—an excellent electrical conduction is maintained also in case of changes in the thickness of the multilayer actuators.

In one particular embodiment, the haemolysator according to the invention comprising an oscillation system with piezoelectric multilayer actuators which have been contacted according to the invention is characterized in that the piezoelectric multilayer actuators are clamped between a first and a second conductor, with electrically conductive mats being arranged at the interfaces between the at least one multilayer actuator and the conductors, the mats containing particles of an electrically conductive material, in particular carbon.

The invention also provides a process for the function testing and monitoring of the operating state of the haemolysator equipped with piezoelectric multilayer actuators by monitoring the electrical parameters of the multilayer actuators. Such function testing and monitoring is advantageous in particular for a haemolysator with a replaceable cuvette. Another advantage of said process is that an optimum operating point or range, e.g., an optimum frequency range and/or an optimum stroke amplitude, of the haemolysator in combination with a cuvette can thereby be found, depending on varying oscillation properties (e.g., by regularly replacing the cuvettes). The process according to the invention for operating a haemolysator according to the invention with oscillation generating elements designed as piezoelectric multilayer actuators is based on the fact that the piezoelectric multilayer actuators are used as sensors by detecting and evaluating physical parameters of the multilayer actuators, utilizing the piezo effect (i.e., the physical phenomenon in which an electrical signal is induced by applying a mechanical pressure load onto a piezo element).

In one embodiment of the process according to the invention, the detected physical parameter is the fading-out of the sonotrode plate after the electrical signal supply has been switched off, with the fading-out manifesting itself in the generation of an electrical voltage signal by the multilayer actuators. A centre frequency and optionally the quality of the oscillating system can be determined from the electrical voltage signal generated by the multilayer actuators using, for example, a Fast Fourier Transformation.

Alternatively, the detected physical parameter is a mechanical force which acts upon the multilayer actuators and is determined by measuring the electrical voltage generated by the multilayer actuators.

It is also envisaged to detect and evaluate the electrical capacity of the multilayer actuators as a physical parameter.

If the evaluation of a detected physical parameter of the piezoelectric multilayer actuators shows that it lies outside of a predetermined operating range, measures of error correction and/or alarms may be initiated.

Figure 3:
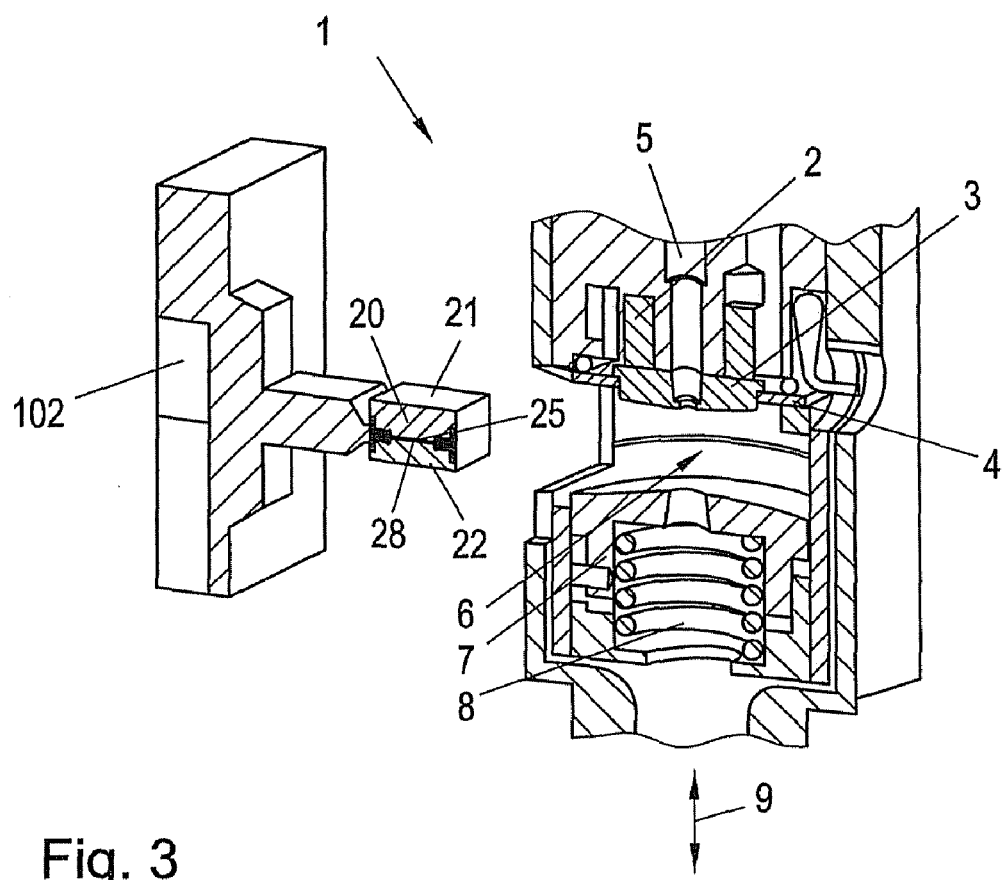
FIG. 3 shows a haemolysator according to the invention as part of a spectroscopic analyzer in perspective view.
Figure 4:
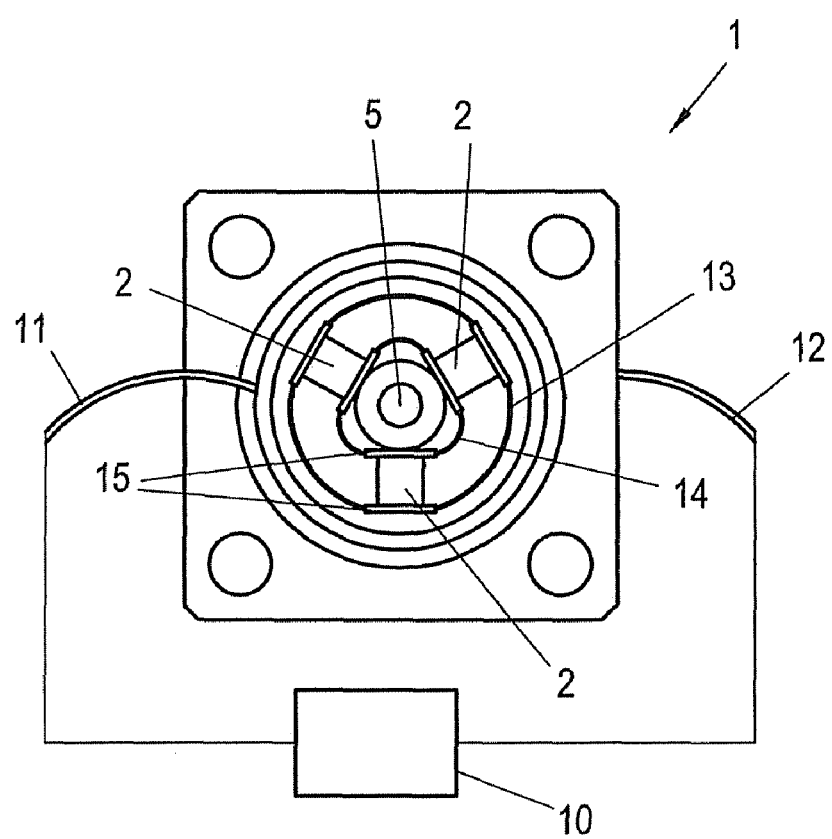
FIG. 4 shows a top view of a haemolysator according to the invention designed with cubical piezoelectric multilayer actuators which are contacted with conductive carbon mats.

A particular embodiment of a haemolysator 1 according to the invention is illustrated in FIG. 3 and FIG. 4. The haemolysator 1 is integrated in a spectroscopic analyzer, which will be described in further detail below. The haemolysator 1 comprises an ultrasonic oscillation generator which exhibits oscillation generating elements 2, which can be activated variably by an electrical AC-signal generator (not illustrated) in a wide frequency band (e.g., from 20-50 kHz), and a sonotrode plate 3 supported by a disk spring 4, onto which sonotrode plate the oscillation generating elements 2 exert mechanical oscillations in the direction of an optical axis 5. The sonotrode plate 3 transmits those mechanical oscillations to a sample chamber 6. A replaceable cuvette 20 is insertable into the sample chamber 6, which cuvette rests with an oscillation-transmitting wall 21 (glass wall, etc.) against the face of the sonotrode plate 3 so that it absorbs the oscillations of the sonotrode plate 3 and passes them on to a liquid blood sample 28 present in the interior of the cuvette, whereby bubbles develop and burst in the blood sample 28 due to cavitation effects, which results in the haemolysis of the blood.

To enable the oscillation transfer to the cuvette 20 to work, a counter weight 7 is arranged on the side of the sample chamber 6 which faces the sonotrode plate 3, which counter weight is moved through a mechanism, which is not further illustrated, as far as to the cuvette 20 after the cuvette 20 has been inserted into the sample chamber 6 and is moved back after the measurements have been conducted (see double arrow 9) in order to release the cuvette. The counter weight 7 presses the cuvette 20 in the clamped state against the sonotrode plate 3. The counter weight 7 is mechanically prestressed by a helical spring 8. The pretensioning force produced by the helical spring 8 should, on the one hand, be small so that the cuvette 20 is not compressed, whereby its sample channel 25 would be squeezed, which would in turn change the optical properties and hence the measuring accuracy. On the other hand, the pretensioning force should not fall below a minimum force so as to prevent the sonotrode plate 3 from lifting off from the cuvette 20 in case of oscillations.

The oscillation generating elements 2 are designed as cubical-shaped piezoelectric multilayer actuators (see FIG. 4) which comprise approx. 180 ceramic layers of a piezoelectric material, which are stacked on top of each other. Each cube has an electrical capacity of approx. 350-500 nF. The layers are mechanically connected in series and connected electrically parallel, whereby they are laterally contacted at opposing edges and undergo changes in length in the direction of the optical axis 5, which add up to a change in the overall length, when they are excited by an electrical AC-signal from an AC-signal generator 10. For the implementation of the haemolysis, an alteration of length of approx. 1 μm to approx. 30 μm, for example approx. 5 μm, is sufficient in most cases. The multilayer actuators are propped up—viewed in the direction of the optical axis—with a first face against a support body of the haemolysator and with the opposite face against the sonotrode plate 3. The multilayer actuators can be arranged radially around the optical axis 5. Alternatively, it might be conceivable to provide a ring-shaped multilayer actuator arranged coaxially with respect to the optical axis.

The capacity of approx. 350-500 nF per multilayer actuator requires currents of several amperes for its triggering. In order to be able to introduce those currents reliably into the multilayer actuators, a specific contacting has been developed, which is now explained with reference to FIG. 4.

The haemolysator 1 comprises an external ring-shaped conductor 13 and an internal triangular or radial conductor 14 made of copper, which are connected via lead wires 11, 12 to an electrical AC-signal generator 10. At least one of the two conductors 13, 14 is designed as a clamping spring. The oscillation generating elements 2 designed as multilayer actuators are clamped between the two conductors 13, 14 while being grouped radially around the optical axis 5, wherein a conductive contact mat 15, in particular a contact mat 15 containing carbon/graphite, is, in each case, arranged between a first side wall of each multilayer actuator and the inner lateral area of the external conductor 13 as well as between a second side wall of each multilayer actuator and the outer lateral area of the internal conductor 14. As a result of mechanical clamping forces, those contact mats 15 are pressed by the external and/or internal conductor(s) 13, 14 against the side walls of the multilayer actuators and, in doing so, penetrate into the unevennesses (pores) of the walls of the multilayer actuators, whereby the contact surface is enlarged many times over. A metal foil, e.g., silver foil, would not show this effect.

The application of the oscillation system illustrated in FIG. 4 which has at least one piezoelectric multilayer actuator as an oscillation generating element 2, with the at least one piezoelectric multilayer actuator being clamped between a first and a second conductor 13, 14, with electrically conductive mats 15 being arranged at the interfaces between the multilayer actuator and the conductors 13, 14, the mats containing particles of an electrically conductive material, in particular carbon, is not limited to the use in the haemolysator, but may advantageously be employed also in other technical fields.

The haemolysator 1 may be operated in different operating modes. The main mode of operation is haemolysis, wherein, at the beginning of the haemolysis, the electrical signal generator 10 typically applies a steep voltage ramp to the oscillation generating elements 2 (multilayer actuators). It has also turned out to be beneficial to wobble the frequency of the electrical signal, e.g., in a range of 200 Hz around the centre frequency, whereby improved haemolysis results can be achieved.

For purifying the system, signals of a greatly varying frequency can be applied to the oscillation generating elements 2, whereby bubbles of greatly different diameters and densities are produced in the liquid sample (wherein a specific cleaning liquid may also be provided as a sample), which substantially improves the cleaning efficiency with regard to different contaminations.

In order to eliminate undesired gas bubbles in the sample channel 25 of the cuvette 20, the gas bubbles can be set in motion and transported from the sample channel 25 by applying an electrical signal of approx. ⅔ of the centre frequency. Furthermore, for this purpose, the optical measuring window of the cuvette may have an appropriate geometrical shape so that those gas bubbles are transported out of the optical measuring range as reliably as possible.

Figure 5:
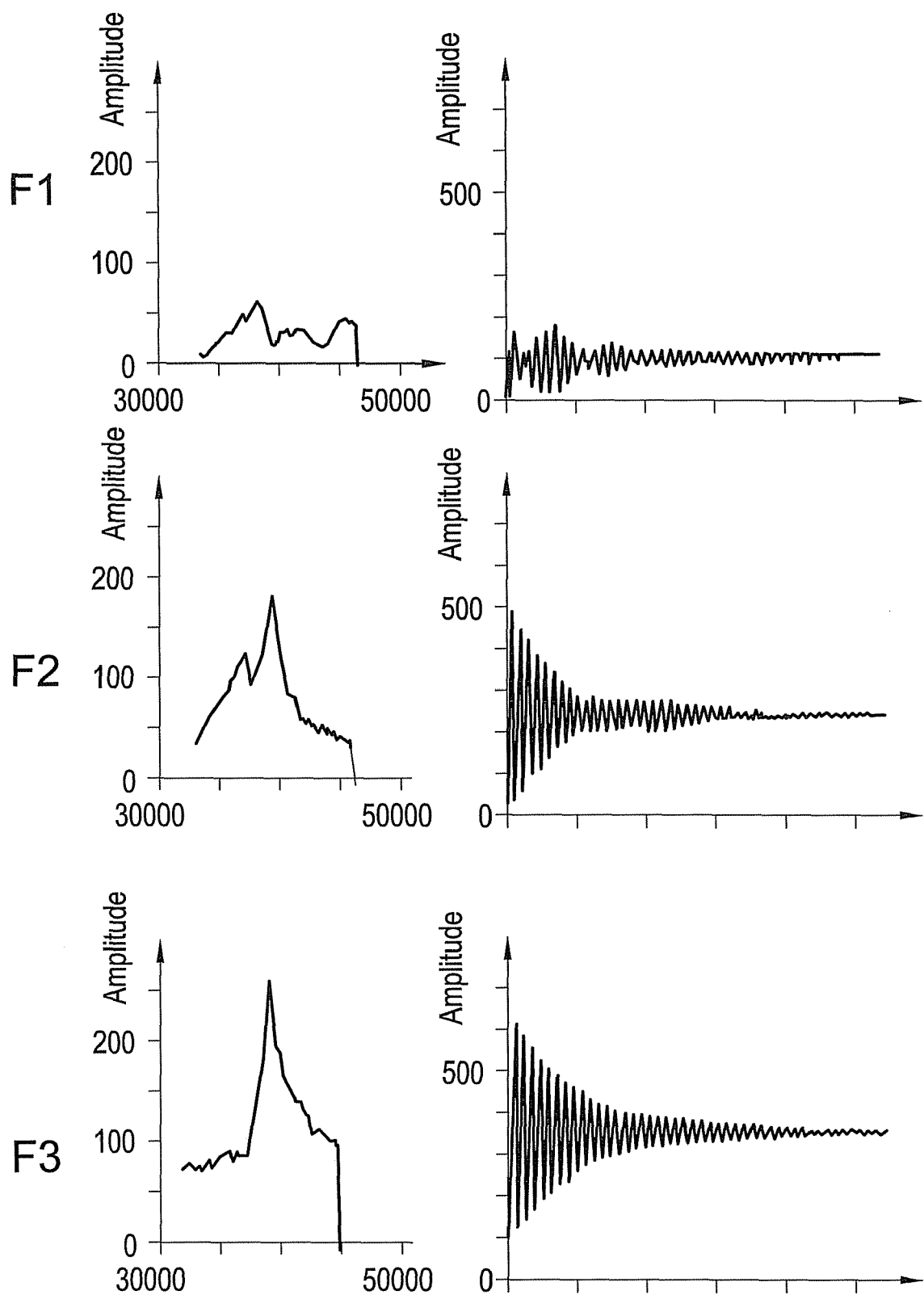
FIG. 5 shows the dynamic response of a haemolysator according to the invention in the time and frequency domains at three different excitation frequencies.

Furthermore, for carrying out inspections and quality checks, the oscillation generating elements 2 designed in the form of piezoelectric multilayer actuators can be used as sensors by detecting and evaluating physical parameters of the multilayer actuators, utilizing the piezoelectric effect. In this way, the dynamic response of the haemolysator 1 and of the total oscillation system, respectively, in the haemolysator is detectable as well. For this purpose, the fading-out process of the sonotrode plate 2 after the electrical signal supply to the multilayer actuators has been switched off is, for example, detected, with the fading-out manifesting itself in the generation of an electrical voltage signal by the multilayer actuators. The centre frequency and optionally the quality of the oscillating system are determined from the electrical voltage signals generated by the multilayer actuators using, for example, a Fast Fourier Transformation. FIG. 5 shows the dynamic response of the haemolysator 1 in the time (on the right, unit of the x-axis in rel. units of time, unit of the y-axis in mV) and frequency domains (on the left, unit of the x-axis in Hz, unit of the y-axis in rel. units) at three different excitation frequencies F1, F2, F3. The upper curve progression (excitation frequency F1) shows a maladjustment of the frequency of the electrical signal generator 10, the medium curve progression (excitation frequency F2) shows an almost correct adjustment of the frequency of the electrical signal generator 10, and the lower curve progression (excitation frequency F3) shows an optimum adjustment of the frequency of the electrical signal generator 10.

Figure 7:
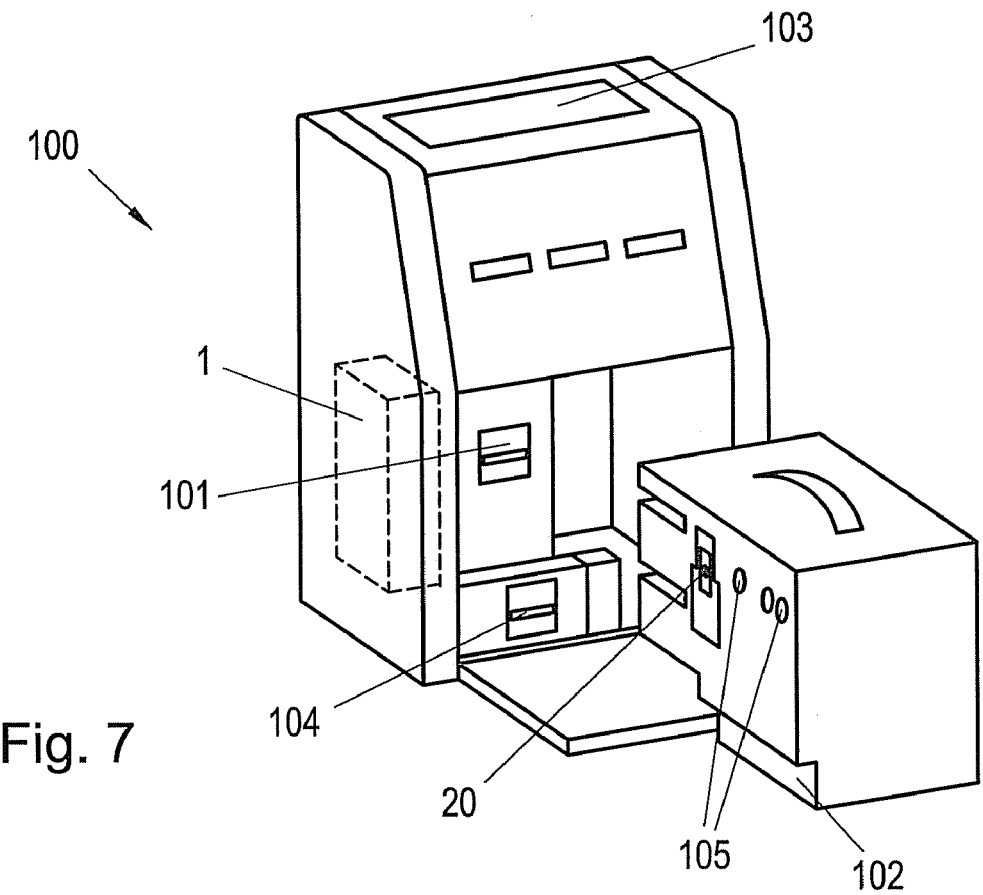
FIG. 7 shows a schematic view of a modularly designed spectroscopic analyzer in which the haemolysator according to the invention is incorporated.

FIG. 7 schematically shows a modular concept of a spectroscopic analyzer 100 in which the above-described haemolysator 1 is used in combination with the cuvette 20. The analyzer 100 is designed so as to be "almost without maintenance" so that all consumption materials required for a continuous operation are present in the form of cassettes and/or modules (so-called "consumables") and therefore can be exchanged also by (technically) untrained personnel. In this exemplary embodiment, the consumption materials used are summarized in the following consumables:

A sensor cassette 101 which contains at least a part or all of the sensors required for the determination of analytes.

A fluid pack 102 containing liquid containers, reagent packs and waste containers containing the functional fluids (e.g., calibration solutions, washing solutions, reference liquids, certain reagent solutions required for the operation . . . ) which are necessary for the operation of the analyzer 100. Optionally, further elements or functionalities such as the entire fluidic system or parts thereof, the sample input device or also further sensory components may likewise be contained in the fluid pack 102. A cuvette 20 including the associated liquid supplying and discharging fluidic paths is integrated in the fluid pack 102, as will be explained in further detail below. This means that the cuvette 20 is regularly replaced with every exchange of the fluid pack 102 (e.g., at intervals of several weeks).

A printer paper cassette 103 for an internal printer.

Optionally a quality control cassette 104 comprising reference solutions in ampule form for conducting an automated quality check, which can be exchanged by the personnel themselves by simple intuitive manipulations.

The categorization of the consumables as described here is only exemplary. It is also conceivable to summarize (partial) functionalities or (partial) elements of several consumables so that, for example, less or even only one consumable is required. On the other hand, it is also conceivable to distribute (partial) functionalities or (partial) elements of individual consumables over several (e.g., over several sensor cassettes or modules). It is, however, an essential basic idea to incorporate the cuvette in one of the consumables which are used so that it is exchangeable together with this consumable.

The consumables are coupled to each other and to the analyzer, respectively, by interfaces aligned to each other, e.g., in the form of fluidic docking fittings 105. The mechanical connection of the consumables to the respective counterparts may occur via a simple manual motion sequence directly by the user or by drives located in the device which perform the coupling automatically after the user has merely brought the cassette into "position".

The blood gas analyzer 100 contains an oximeter module in which, using a spectroscopic measuring process, the concentrations of the haemoglobin derivatives $O_2Hb$, HHb, COHb, MetHb, as well as the blood parameter tHb (total haemoglobin), $SO_2$ (oxygen saturation) and bilirubin of the sample located in the cuvette 20 are determined. In doing so, characteristic absorption properties of those substances are utilized and the measurands are evaluated via a mathematical algorithm. In order to be able to achieve the required measuring accuracy, a haemolysis of the whole blood is in most cases necessary prior to the optical measurement. For performing the haemolysis, the schematically indicated haemolysator 1 is integrated in the oximeter module. Furthermore, the oximeter module includes—similarly to what is illustrated in FIG. 1—a lamp unit comprising (a) light source(s), fluidic supply and discharge lines, a light conductor which supplies the light generated in the lamp unit to the cuvette 20 and a light conductor which collects the light which has passed through the sample in the cuvette 20 and passes it on to a polychromator, which effects a spectral separation of the received light, as well as a detector for evaluating the spectral ranges of the received light. The haemolysator 1 is designed such that the cuvette 20 as part of the consumable 102 is inserted into the haemolysator 1 when the consumable 102 is introduced into the analyzer 100 and is removed from the haemolysator 1 when the consumable 102 is withdrawn from the analyzer 100. By this construction, clogging problems are avoided in oximeter modules of known analyzers in which an optical measuring chamber (cuvette) is designed as an integral component of the analyzer which remains permanently in the device.

Figure 6A:
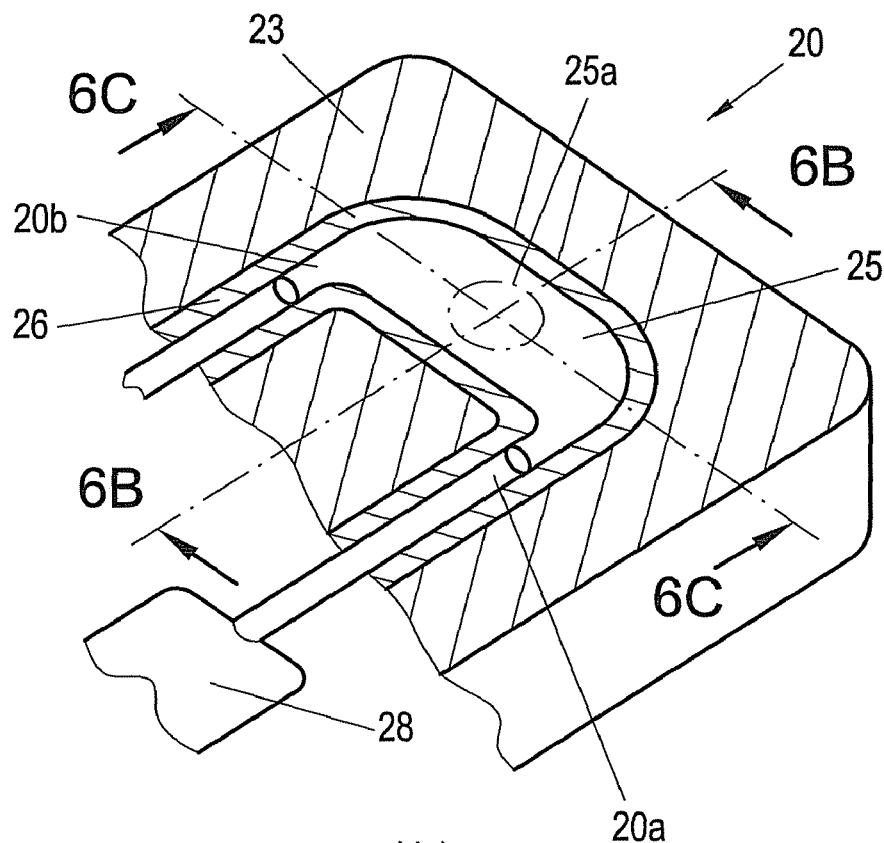
FIG. 6A, FIG. 6B and FIG. 6C show a particular embodiment of a cuvette used in combination with the haemolysator according to the invention in an isometric view, in a sectional view taken along line 6B and in a sectional view taken along line 6C of FIG. 6A, respectively.
Figure 6B:
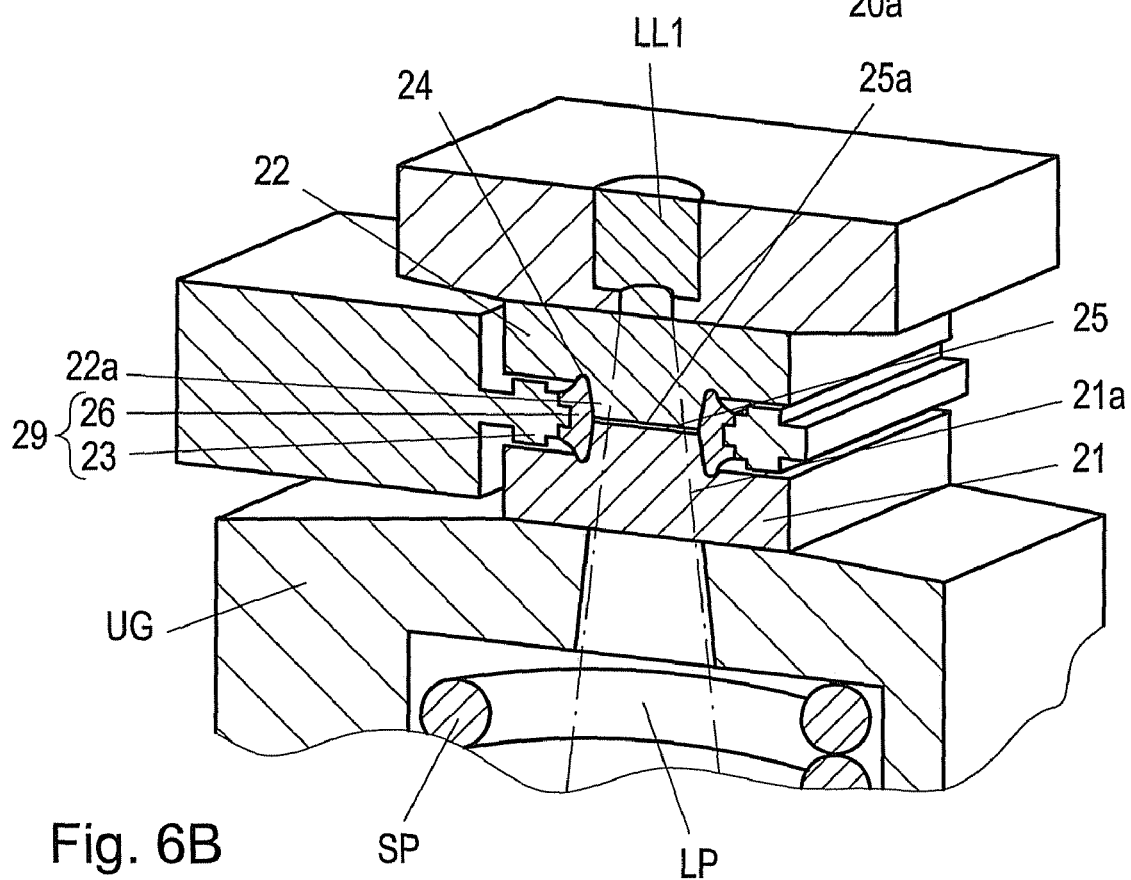
Figure 6C:
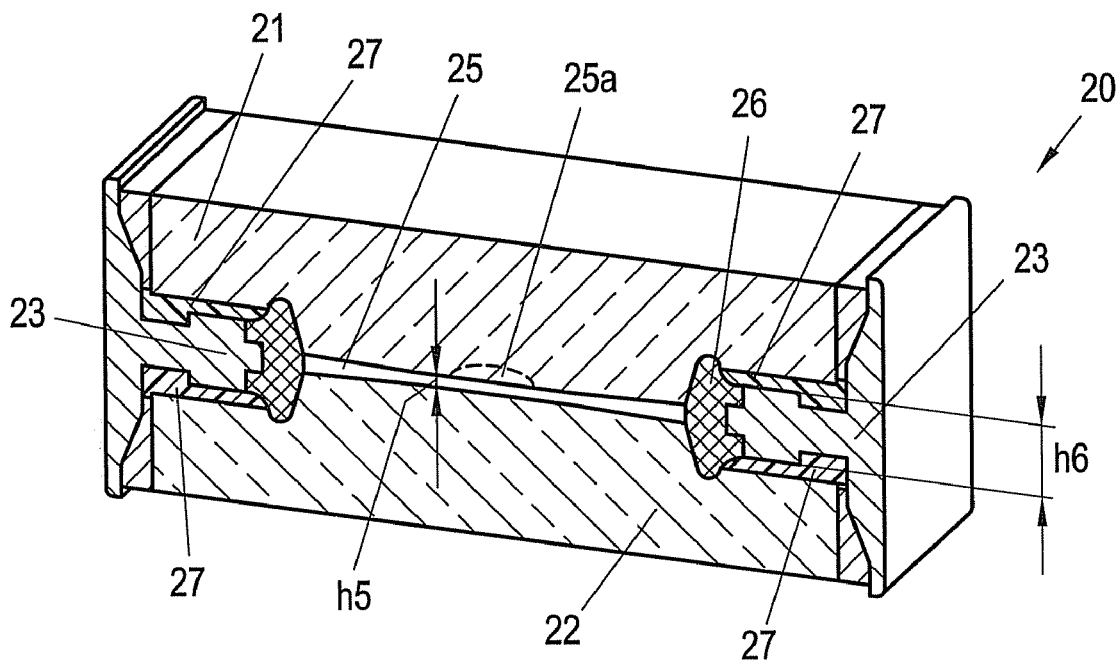

By reference to FIG. 6A, FIG. 6B and FIG. 6C, the design of the cuvette 20 is now explained. The cuvette 20 comprises a spacer 23, a first and a second transparent element 21, 22 and a sealing element 26. The two transparent elements 21, 22 each have a shoulder 21a, 22a and are arranged opposite to each other on the spacer 23 in such a way that the two shoulders 21a, 22a face each other and extend into a channel-shaped recess 24. Thereby, the faces of the shoulders 21a, 22a have a distance between each other which corresponds to a defined height of a sample channel 25 formed between the faces of the shoulders 21a, 22a. The sample channel 25 is sealed around its circumference by a sealing element 26, with the sealing element 26 resting against the lateral areas of the shoulders 21a, 22a and pushing into the gap therebetween. The sealing element 26 comprising the spacer 23 is formed as a combination element 29, e.g., a 2-component injection-moulded part or a composite pressed part. This provides essential advantages for the assembly of the cuvette 20. In order that the cuvette 20 exhibits a suitable strength for ultrasonic applications, the spacer 23 is manufactured from an injection-mouldable synthetic material having high modulus of elasticity values of, for example, more than 2500 MPa, or more than 5000 MPa.

The transparent elements 21, 22 are made of glass, typically pressed glass, which can be processed readily. Alternatively, they are manufactured from a synthetic material exhibiting the following properties: low strain birefringence, minor creep behaviour, no/low gas permeability, chemical resistance, thermostability, optical transparency in the visible (VIS) and near infrared (NIR) wavelength ranges. The visible range (VIS) is defined as the wavelength range between 380 and 780 nm; the near infrared range (NIR) is between 780 and 1400 nm. In one example, the transparent elements are composed of synthetic materials from the group of thermoplastic olefin polymers.

The sealing element 26 consists of an elastomer, typically having a Shore D-hardness of between 50 and 80, for example a Shore D-hardness of between 60 and 70.

The sample channel 25 exhibits an optical measuring range 25a in which the transparent elements 21, 22 are arranged so as to be plane-parallel. In order to avoid edge effects, the optical measuring range 25a is spaced apart from the edge of the sample channel 25. A light conductor LL1 leads close to the measuring range 25a and emits light through the measuring range 25a along the light path LP, which light is spectroscopically analyzed after having passed through the measuring range 25. Alternatively, reflective optical measuring systems are provided as well.

The sample channel 25 has an arched design so that the inlet 20a for the sample 28 and the outlet 20b lie on the same side, which involves the advantage of a reduced construction volume. In addition, the replaceable applicability of the cuvette can thus be facilitated, since all fluidic connections are on one side. Furthermore, it should be noted that the width of the sample channel 25 tapers from a central region comprising the measuring range 25a toward the inlet 20a and toward the outlet 20b, while the height of the sample channel increases so that the cross-sectional area of the sample channel 25 remains essentially constant across its length. In this way, the formation of swirls in the sample 28 is prevented in the sample channel 25. For the same purpose, the sample channel 25 exhibits only constant changes in the channel.

For assembling the cuvette 20, the two transparent elements 21, 22 can be glued to the spacer 23. As an alternative, pressing or plugging is also recommendable in this embodiment.

Figure 2:
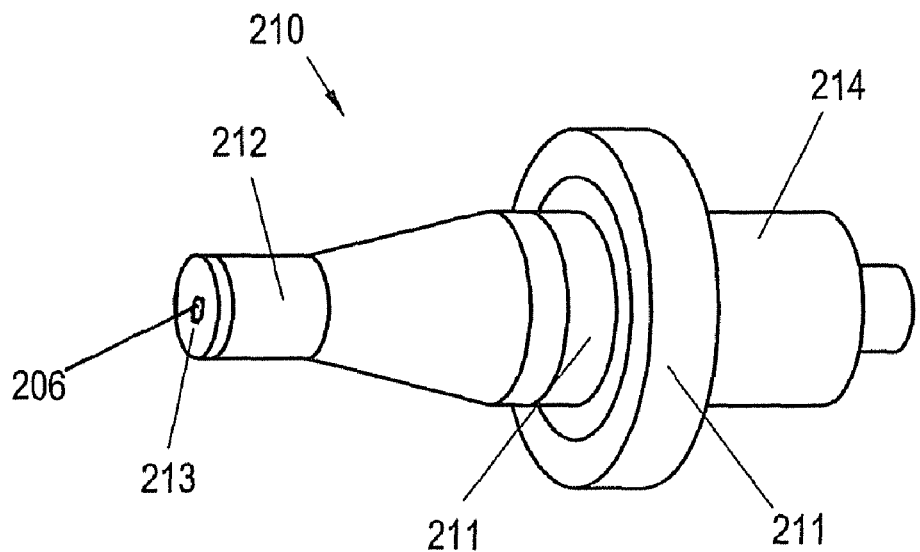
FIG. 2 shows a perspective illustration of a known ultrasonic transducer haemolysator based on the resonance oscillator principle.

In FIG. 6C, which shows a longitudinal section through the sample channel 25, it can best be seen that the sample channel 25 has inflow bevels conically tapering toward the measuring range 25a and, in the measuring range 25, displays a plane-parallel course of the surfaces of the transparent elements 21, 22 which define the sample channel. Furthermore, adhesive layers 27 can also be seen in FIG. 2C, to which the spacer 23 with the two transparent elements 21, 22 is glued. The adhesive is an adhesive which is dimensionally stable after curing so that the adhesive layers 27 exhibit a defined thickness.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A haemolysator comprising a sonotrode plate that transmits mechanical oscillation to a sample chamber, an oscillation generating element that is set into mechanical oscillation by an electrical AC-signal generator and is excitable toward mechanical oscillations in a wide frequency band, and an exchangeable cuvette that is insertable into the sample chamber, wherein the cuvette comprises a sample channel for receiving a sample to be haemolysed, the channel comprising at least one oscillation-transmitting wall resting against the sonotrode plate when the cuvette inserted into the sample chamber.

2. The haemolysator of claim 1, wherein the oscillation generating element is tunably excitable.

3. The haemolysator of claim 1, wherein the oscillation generating element is excitable toward mechanical oscillation while being adjustable in its stroke amplitude.

4. The haemolysator of claim 1, further comprising two transparent elements that are spaced apart from each other to define two opposing boundary surfaces of the sample channel and at least one sealing element defining side walls of the sample channel.

5. The haemolysator of claim 4, wherein the sample channel is closed in the longitudinal direction and comprises an inlet and an outlet, and wherein at least one spacer keeps the transparent elements apart from each other.

6. The haemolysator of claim 5, wherein at least one of the two transparent elements has a shoulder extending in the direction toward the other transparent element and forms a boundary surface of the sample channel so that the height of the sample channel is smaller than the height of the at least one spacer.

7. The haemolysator of claim 4, wherein the cuvette is integrated in a consumable of a spectroscopic analyser.

8. The haemolysator of claim 7, wherein the consumable is a fluid pack comprising functional liquids and/or waste containers.

9. The haemolysator of claim 1, wherein the oscillation generating element is a piezoelectric multilayer actuator.

10. The haemolysator of claim 9, wherein the electrical AC-signal generator generates non-sinusoidal signals.

11. The haemolysator of claim 10, wherein the non-sinusoidal signals comprise freely definable waveforms and/or signals tunable in frequency.

12. The haemolysator of claim 9, wherein the piezoelectric multilayer actuator is clamped between a first and a second conductor and further comprises electrically conductive mats arranged at the interfaces between the piezoelectric multilayer actuator and the conductors, the mats comprising particles of an electrically conductive material.

13. The haemolysator of claim 12, wherein the electrically conductive material is carbon.

14. The haemolysator of claim 1, wherein the frequency band comprises frequencies ranging from 20-50 kHz.

15. A spectroscopic analyzer for the spectroscopic analysis by irradiating a sample with a beam of light and detecting the spectrum of the beam of light after it has passed through the sample, wherein the a sample located in a cuvette that is at least partially transparent, the analyzer comprising the haemolysator of claim 1 to haemolyse the sample.

16. A process for operating the haemolysator of claim 9 comprising tuning the piezoelectric multilayer actuator from 20 to 50 kHz.

17. The process of claim 16, wherein the piezoelectric multilayer actuator is excitable toward mechanical oscillations is a sensor for detecting and evaluating a physical parameter associated with a piezo effect.

18. The process of claim 16, wherein a detected physical parameter is the fading-out of the sonotrode plate after the electrical signal supply has been switched off.

19. The process of claim 18, wherein the fading-out manifests itself in the generation of an electrical voltage signal by the multilayer actuator.

20. The process of claim 18, wherein a centre frequency is determined from the electrical voltage signal generated by the multilayer actuator.

21. The process of claim 20, wherein the centre frequency is determined using a Fast Fourier Transformation.

22. The process of claim 17, wherein the detected physical parameter is a mechanical force that acts upon the multilayer actuator and is determined by measuring the electrical voltage generated by the multilayer actuator.

23. The process of claim 17, wherein the detected physical parameter is the electrical capacity of the multilayer actuator.

24. The process of claim 17, wherein the haemolysator initiates at least one of an alarm or error correction if a detected physical parameter lies outside of a predetermined operating range.

* * * * *